United States Patent
Given

(10) Patent No.: US 8,517,606 B2
(45) Date of Patent: Aug. 27, 2013

(54) POLAR COMPONENT DETECTION

(75) Inventor: Russell M. Given, Calgary (CA)

(73) Assignee: Transcanada Pipelines Limited, Calgary, Alberta (CA)

( * ) Notice: Subject to any disclaimer, the term of this patent is extended or adjusted under 35 U.S.C. 154(b) by 9 days.

(21) Appl. No.: 13/290,661

(22) Filed: Nov. 7, 2011

(65) Prior Publication Data

US 2012/0128032 A1     May 24, 2012

(51) Int. Cl.
*G01K 7/02*     (2006.01)
*G01K 7/22*     (2006.01)
*G01K 13/00*     (2006.01)

(52) U.S. Cl.
USPC ............. 374/179; 374/45; 374/141; 374/183; 374/185

(58) Field of Classification Search
USPC ................ 374/141, 109, 100, 179; 73/19.01, 73/23.2
See application file for complete search history.

(56) References Cited

U.S. PATENT DOCUMENTS 6,015,484 A * 1/2000 Martinchek et al. ....... 205/775.5
6,155,098 A * 12/2000 Shapiro et al. ............... 73/29.01
7,679,059 B2    3/2010 Zhou

OTHER PUBLICATIONS

Standard Test Method for Water Vapor Content of Gasous Fuels by Measurement of Dew-Point Temperature, ASTM, Designation D1142-95, 2006.

* cited by examiner

*Primary Examiner* — Lisa Caputo
*Assistant Examiner* — Brandi N Hopkins
(74) *Attorney, Agent, or Firm* — Kenneth H Johnson

(57) ABSTRACT

In a hydrocarbyl gas the presence and amount of a condensable polar component may be detected by voltage or current excursions over background noise as measured using a probe having at least two common electrodes and optionally a third electrode preferably inert to corrosion.

5 Claims, 3 Drawing Sheets

POLAR COMPONENT DETECTION

FIELD OF THE INVENTION

The present invention relates to a process to qualitatively (±10%) identify existence of condensable polar components in a hydrocarbon. More particularly the present invention relates to a process to qualitatively (±10%) identify the water vapor content in a stream of natural gas inside a gas transmission pipeline.

BACKGROUND OF THE INVENTION

Prior Art

In the transmission and distribution of natural gas the gas quality specifications must be met. The gas quality specifications (tariff) specify the energy value and purity of the gas required for the end consumer. The impurity limitations also reduce the potential of internal corrosion occurrence of the transmission and distribution piping. A gas processing plant typically extracts impurities from the gas stream. One of the impurities which require limitation in a natural gas stream is water vapor. Water vapor at its dew point pressure and temperature conditions condenses. Liquid water is an electrolyte promoting corrosion reactions in a pipeline.

There are a number of methods to measure the dew point of a mixture of gasses.

One method of measuring the moisture content of a mixture of hydrocarbon gasses is to measure the dew point of water in the mixture by passing the gas over a chilled mirror (ASTM D1142). The mirror is chilled and the water vapor condenses on the mirror at or below the dew point of the mixture. The mirror is cycled through a warming and cooling cycle and at the dew point water condenses on the mirror reducing its reflectance. When a reduction in reflectance is detected the temperature is noted and the dew point is noted. The dew point is a function of partial pressure of water vapor in the gas mixture so the partial pressure or amount of water vapor in the mixture may be estimated. The exact point when water starts to condense on the mirror is difficult to determine even with automated systems. The error in the measurement may be large, particularly if hydrocarbons in the mixture start to condense at about the same temperature as water under the conditions of measurement. As a result this type of system typically requires manual operation by a skilled technician which is not required by the present invention. Manual operation at a sensing site is not applicable for remote sensing.

Another potential route to determine the water content of a mixture of hydrocarbon based gas is the use of a silicon oxide sensor and reflected light. The sensor absorbs water into its upper layers changing how light is reflected off the surface of the sensor. The change in wavelength of the reflected light can be correlated to the moisture concentration in the gas. Again the system may suffer from contamination with hydrocarbon condensation.

Relative changes in moisture content of a mixture of gases may be determined by measuring the adsorption of water on a hygroscopically coated quartz crystal oscillator. As the mass of the crystal changes due to adsorption of water so does the resonance frequency of the quartz crystal. This type of system is fairly complicated as it requires driers for the surface of the crystal, permeation tubes and sample line switching. Also the presence of glycols and other polar molecules may interfere with the system. These systems appear to be labour intensive requiring maintenance for the hygroscopic surface, the driers and switching mechanism. This is not an ideal system for use in remote locations.

U.S. Pat. No. 7,679,059 issued Mar. 16, 2010 in the name of Zhou assigned to SpectraSensors, Inc. teaches the use of differential absorption harmonic spectra to quantify low concentrations of water vapor in a sample of gaseous olefins. The sample spectrum is compared to that of a dehydrated sample to remove components relating to background materials. The revised harmonic spectrum of the sample is then compared to the first to determine the amount of water vapor in the sample. The system does not appear useful for analysis of natural gas samples.

There are a number of patents relating to the use of electrochemical noise to detect corrosion in piping and reactors. These patents correlate the amount of electrochemical noise to the amount of corrosion or pitting proximate the probe. Generally the probe is immersed in a conductive medium (an electrolyte). The probe comprises at least two common electrodes, typically made of the material being tested for corrosion (e.g. carbon steel). Generally the current between the two electrodes is measured using a zero resistance ammeter which may interface with a data acquisition means (e.g. a lap top computer or a remote CPU). Optionally, there may be a third sensor, typically made of a material which is substantially inert to corrosion, such as platinum. The voltage across one of the two common probes and the third (platinum) probe is measured using a voltmeter. From the current and voltage readings one may infer a degree of corrosion proximate to the device. There is nothing in the references to suggest that the electrochemical noise could be used to detect water vapor levels in an organic fluid (gas).

Representative of this art are U.S. Pat. No. 5,139,627 issued Aug. 18, 1992 in the name of Eden et al assigned to Capcis Limited; U.S. Pat. No. 7,520,975 issued Apr. 21, 2009 in the name of Eden assigned to Honeywell International Inc.; and U.S. Pat. No. 6,264,824 issued Jul. 24, 2001 in the name of Reid et al., assigned to Integriti Investments Ltd.

The present invention seeks to provide a robust simple method to determine the dew point and qualitative amount (±10% volume) of polar components (e.g. water) in a hydrocarbon gas, and possibly to give a qualitative indication of corrosion rate (proximate the probe).

SUMMARY OF THE INVENTION

The present invention provides a method to qualitatively determine the content of a condensable polar component in a hydrocarbyl gas at a predetermined temperature and pressures in a vessel or conduit, comprising contacting at least a portion of the gas with a probe comprising a steel housing having an inlet and an outlet for said gas, a high pressure coupling on said housing adapted to receive and cooperate with a probe, comprising at least two common electrodes together with connecting leads from said electrodes to a zero resistance ammeter or a voltmeter, and a temperature sensing device, a temperature controlling device for the probe comprising determining a spike in current or voltage across said two common electrodes for electrochemical noise above a base line.

In a further embodiment the device further includes a data acquisition device including an ammeter and a volt meter optionally with an output to a remote location.

In a further embodiment of the present invention the predetermined temperature of the gas is from −15° C. to 10° C.

In a further embodiment of the present invention the predetermined pressure of the gas is from 3.4 kPa (500 psi) to 20.7 kPa (3000 psi).

In a further embodiment of the present invention the temperature measuring device is selected from the group consisting of a thermocouple and a thermistor together with connecting leads.

In a further embodiment of the present invention the temperature measuring device is used to control the temperature controlling device to keep the probe at a set temperature±0.5°.

In a further embodiment of the present invention said probe further comprises a third electrode together with associated connecting lead.

In a further embodiment of the present invention further comprises measuring the voltage across one of the common electrodes and the third electrode.

In a further embodiment of the present invention the value of the voltage across two common electrodes is compared to calibration data relating voltage (above background noise) to polar component vapor concentration in the gas over predetermined pressure and temperature ranges.

In a further embodiment of the present invention the value of the voltage across one of the common electrodes and the third electrode is compared to calibration data relating voltage (above background noise) to polar component vapor concentration in the gas over predetermined pressure and temperature ranges.

In a further embodiment of the present invention said third electrode is selected from the group consist of platinum, palladium; nickel, copper, silver, gold, ruthenium, rhodium and alloys thereof.

In a further embodiment of the present invention the leads from said electrodes are connected to a data acquisition device.

In a further embodiment of the present invention said data acquisition device is a remote central processing unit (CPU) which also stores the calibration data.

In a further embodiment of the present invention said gas is natural gas.

In a further embodiment of the present invention said polar component is water.

In a further embodiment of the present invention the temperature of the gas is from −12° to −8° C. and the pressure is from 4.1 kPa (600 psi) to 6.9 kPa (1000 psi).

The present invention also provides a device for detecting water in an amount of at least 65 mg per standard cubic meter at pressures up to 30 MPa and a temperature from −15 to 0° C. in a $C_{1-8}$ hydrocarbyl gas in a container said device comprising a housing having an entrance and an exit into said container, a cross connection, a probe comprising at least two common electrodes and associated leads which is sealably inserted into one side of the cross connection, a temperature sensing device and associated leads sealably inserted into the other side of said cross connection so that the temperature sensing device touches the surface of said probe and a temperature control device to maintain the temperature of the probe at ±0.5° C. of a set temperature. Optionally the device may further include a pressure sensor or a pressure transducer together with a pressure reading transmission device.

The present invention further comprises any combinations, in whole or in part of the above embodiments and further including disclosures below.

DETAILED DESCRIPTION

Figure 1:
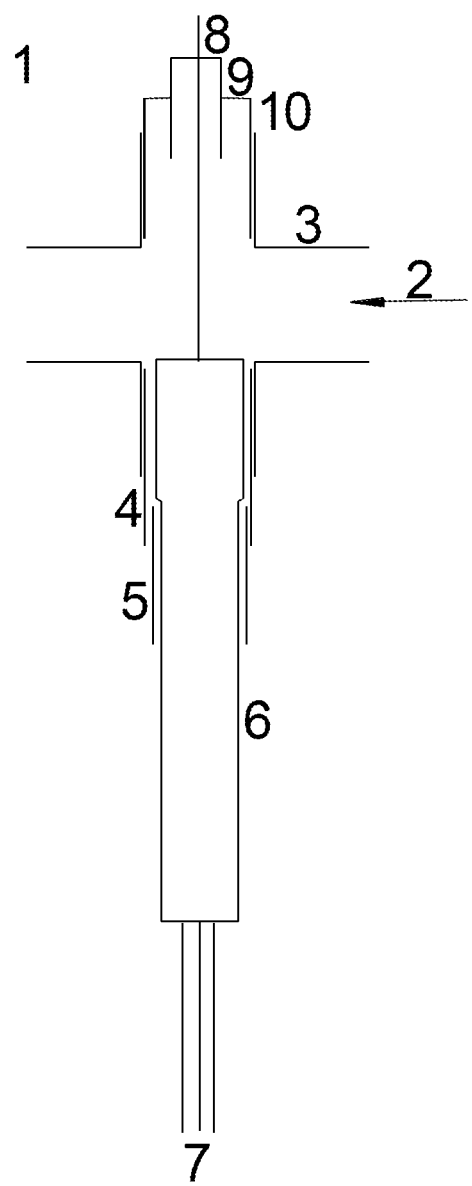
FIG. 1 is schematic sectional view of a probe of the present invention installed on a pipeline.

In FIG. 1, the probe is mounted on a housing 1, only partially shown, attached to a gas pipeline to permit a flow of gas through the housing in the direction indicated by arrow 2. The housing contains a cross connection 3. One side of the cross connection is a housing for the probe comprises nipples 4 and 5 attached to the wall of the housing which receives a probe 6. In the figure the probe is a three electrode probe having two common electrodes, typically carbon steel and an inert, typically platinum, electrode with a glass end cap seal. The probe is filled with epoxy and three electrodes 7 extend from the end of the probe. While the figure shows a three electrode probe the probe could be a two electrode probe in which both electrodes are the same and of the same material of the pipeline (carbon steel). The other side of the cross connection 3 is a housing for a thermocouple 8 which extends towards and touches the face of probe 6. Bushing 9 and connector 10 hold the thermocouple in place.

The fittings for the cross connection are typically made of stainless steel.

The thermo couple could be replaced with a device of equivalent functionality, such as, a thermistor.

The thermocouple or thermistor may be attached to any suitable data acquisition system such as or including a voltmeter. The output from the thermocouple or thermistor is used to control a heating/cooling device (not shown) to maintain the surface of the probe at a constant temperature, generally within ±0.5° C. of the set temperature. The set temperature is typically in the range from −35° C. to 15° C., preferably from −15° C. to 10° C., most preferably from −12° C. to −8° C., desirably −10° C. depending on the system pressure. Typically the system will operate at pressures from about 3.4 kPa (500 psi) to 20.7 kPa (3000 psi), preferably from 4.1 kPa (600 psi) to 6.9 kPa (1000 psi). Under these conditions the maximum amount of water vapor in the hydrocarbon (e.g. natural gas) should not exceed about 65 mg of water per standard cubic meter of gas at 101.3 kPa and 15° C. (4 lb of water per million standard cubic feet of gas at 14.65 PSA and 60° F.). If this amount of water vapor is not exceeded there should be no condensation of water from the gas and there will be no current between the two common electrodes (i.e. the base line is zero).

The leads 7 from the electrodes are fed to a data acquisition device. The output from the two common steel electrodes is preferably fed to a zero resistance ammeter. The electrochemical noise is identified as the measured current from the two common electrodes. The output from the optional third (platinum) electrode and one of the common electrodes is preferably fed to a voltmeter. The voltage may be compared to a calibration curve to (qualitatively (e.g. ±10%)) indicate the amount of water vapor in the gas stream.

In one embodiment, depending on the pipeline pressure and the gas quality specifications, the present invention's apparatus can be set to a desired threshold. When the content of water vapour in the gas stream is below the set threshold (i.e. the dew point) the measured current is zero or close to zero. Once the concentration of water vapors in the gas reaches the set threshold (e.g. the dew point and the water condenses) the electrochemical noise spikes upward and remains there due to the existence of liquid water (electrolyte) between the two common electrodes and the energy of the corrosion reactions.

The same is true for voltage measurements across the common electrodes or a common electrode and a third optional electrode. When water vapor content in the gas stream is below the threshold the voltage is a baseline (typically approaching zero). When the content of water vapor in the gas rises above the threshold the voltage spikes identifying the formation of the electrolyte between the electrodes.

Typically the current and voltage may be measured in microamps and volts respectively. The spike in the current can be a 10 volt response and the current spikes up to 4 nanoamps. These values may be used individually or in combination to detect the presence of water vapour in amounts higher than that typical gas specifications would allow. Additionally, the current may also be used to estimate the corrosion of the vessel (pipeline) adjacent the probe.

Advantageously for pipelines the probe may be connected to a centralized data acquisition unit (computer server). This permits probes to be used in remote locations without the need of in-situ presence as the data can be monitored from a central location.

The process of the present invention may be applied to any vessel or conduit holding a hydrocarbon (hydrocarbyl) gas. Typically the hydrocarbon gas will comprise not less than 95 weight %, preferably 98 weight % most preferably 99.5 weight % of one or more $C_{1-4}$ hydrocarbons, preferably methane, ethane and propane and mixtures thereof. While the invention has been described above relative to pipelines it is also applicable to chemical processing of hydrocarbons where very low amounts of polar components, such as water, are specified for the hydrocarbons, such as monomers (e.g. $C_{2-8}$ olefins, preferably $C_{2-6}$ olefins) etc.

Typically the polar component is water.

The two common electrodes may be selected from the same material as the construction of the pipeline or vessel (e.g. carbon steel). However, as the electrodes are isolated from the vessel or pipeline they could be the other material based on sensitivity and robustness. For example stainless steel or other steel electrodes might be used.

The third electrode is made from a material which is inert to corrosion in the given environment. Typically it may be selected from the group consisting of platinum, palladium; nickel, copper, silver, gold, ruthenium, rhodium and alloys thereof made from a material which is inert to corrosion in the given environment. Typically the third electrode is made of platinum.

EXAMPLE

The present invention is illustrated by the following non limiting example

Example 1

Figure 2:
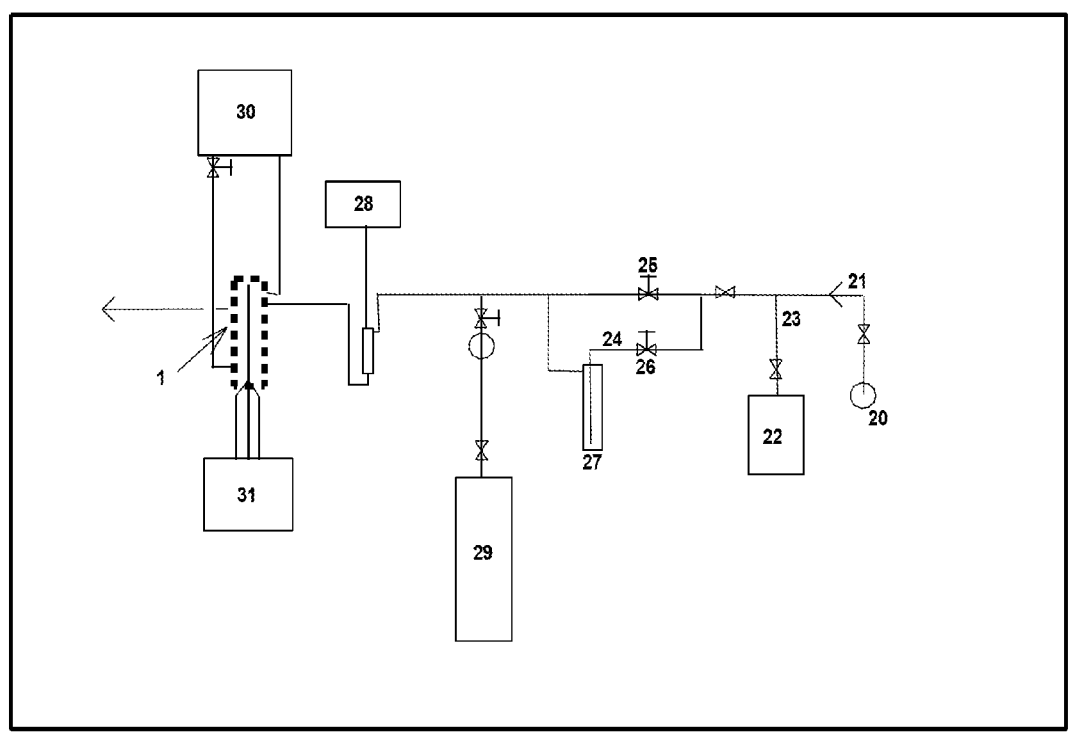
FIG. 2 is a schematic diagram of the water saturation line used in the experiment.

The apparatus for the experiment is shown schematically in FIG. 2. A probe 1, as described above was attached to a high pressure gas line 20, operating at a pressure of about 5500 KPa by line 21. A high pressure syringe pump 22 was attached to line 20 by line 23. A side line 24 was split off line 21 and two metering valves 25 and 26 were used to flow gas through a water saturation bubbler, device 27. A high pressure $CO_2$ cylinder 29 was connected to line 21 down stream of the water saturation device. The line 21 passed through a conventional moisture analyzer 28 and then through a probe 1 of the present invention. The temperature of the probe was controlled by a circulating glycol temperature controller. 30. The leads from the probe were connected to a data acquisition device 31.

Figure 3:
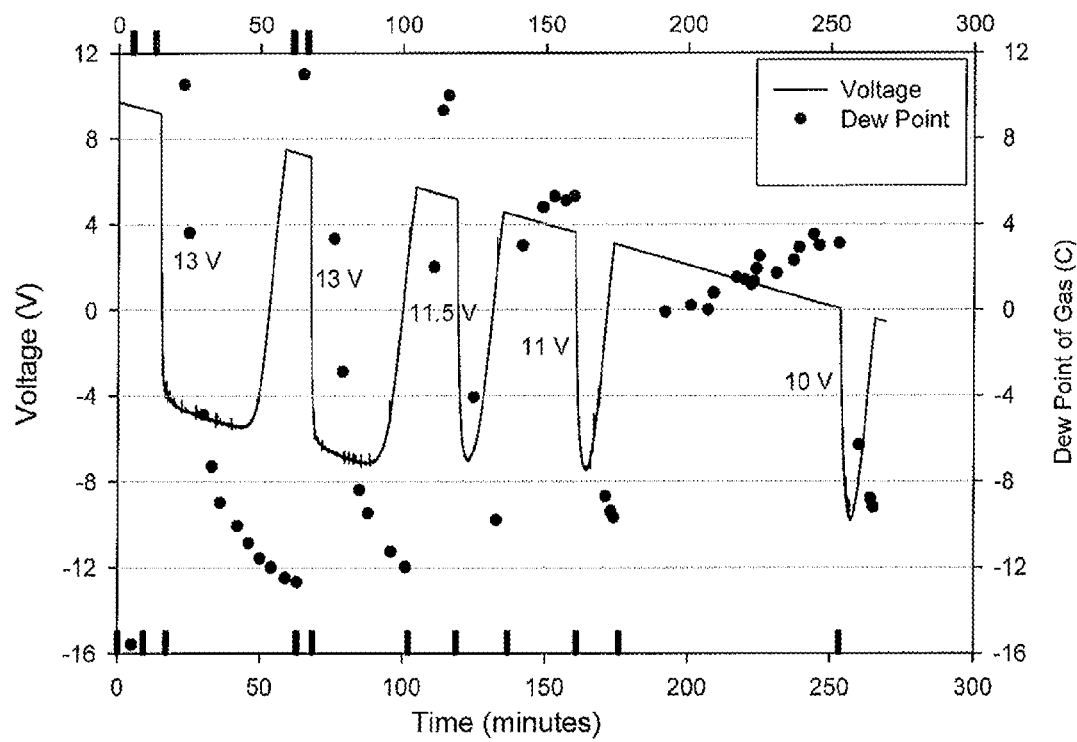
FIG. 3 is a plot of voltage across a common electrode and an inert electrode and varying water vapor content (dew point) of natural gas at substantially constant pressures and temperatures.

The probe was exposed to gas at a substantially constant temperature and pressure having different amounts of water vapor there in (e.g. different dew points) and the valve 26 to the water saturation device was closed so that the water vapour level in the gas dropped. This was repeated a number of times and a plot of voltage against dew point (water vapor in the gas) was made. This is shown as FIG. 3. In the figure the base line is the flat sloping line at the upper part of the curve. The voltage excursion is a result of (reaction to) the gas saturated with different amounts of water (i.e. how much water is in the gas at that temperature and pressure). The bottom of the peaks are a basis for calibration of the voltage excursion to the dew point of the gas. If a line is drawn through the bottom of the valleys a calibration for voltage and dew point may be obtained.

What is claimed is:

1. A method to qualitatively determine the content of a condensable polar component in a hydrocarbyl gas at a temperature from −12° C. to −8° C. and pressure from 4.1 kPa (600 psi) to 6.9 kPa (1000 psi) in a vessel or conduit, comprising contacting at least a portion of the gas with probe consisting of:
   (i) a steel housing having an inlet and an outlet for a gas,
   (ii) a high pressure coupling on said housing adapted to receive and cooperate with a probe consisting of:
      (a) two common carbon steel electrodes
      (b) a third electrode selected from the group consist of platinum, palladium;
   nickel, copper, silver, gold, ruthenium, rhodium and alloys thereof;
      (c) leads from said electrodes to one or more of a zero resistance ammeter and a voltmeter;
      (d) a temperature measuring device selected form the group selected from the group consisting of a thermocouple and a thermistor together with connecting leads; and
      (e) a temperature controlling device for the probe at temperature ±0.5° C. of a set temperature and measuring one or more of
         (i) the voltage across the two common electrodes,
         (ii) the voltage across one common electrode and the third electrode
         (iii) the current across the two common electrodes; and
         (iv) the current across one common electrode and the third electrode;
   and comparing the values to calibration data relating voltage current or both to polar component vapor concentration in the gas over predetermined pressures and temperature ranges.

2. The method according to claim 1, wherein the leads from said electrodes are connected to a data acquisition device.

3. The method according to claim 2, wherein said data acquisition device is a remote central processing unit which also stores the calibration data.

4. The method according to claim 3, wherein said gas is natural gas.

5. The method according to claim 4 wherein said polar component is water.

* * * * *